(12) United States Patent
Pado (10) Patent No.: US 7,426,447 B2
(45) Date of Patent: Sep. 16, 2008

(54) METHOD AND SYSTEM FOR MONITORING STRUCTURAL DAMAGE

(75) Inventor: Lawrence E. Pado, St. Charles, MO (US)

(73) Assignee: The Boeing Company, Chicago, IL (US)

( * ) Notice: Subject to any disclaimer, the term of this patent is extended or adjusted under 35 U.S.C. 154(b) by 462 days.

(21) Appl. No.: 11/199,622

(22) Filed: Aug. 9, 2005

(65) Prior Publication Data
US 2007/0034009 A1 Feb. 15, 2007

(51) Int. Cl.
*G06F 19/00* (2006.01)
(52) U.S. Cl. ........................... 702/109; 342/352
(58) Field of Classification Search .......... 702/109, 702/182–185, 188; 342/352, 357.01, 357.03, 342/357.08
See application file for complete search history.

(56) References Cited

U.S. PATENT DOCUMENTS 5,195,046 A 3/1993 Gerardi et al.
6,006,163 A * 12/1999 Lichtenwalner et al. ....... 702/36

FOREIGN PATENT DOCUMENTS

WO WO2005031501 A2 4/2005

OTHER PUBLICATIONS

PCT Intl Search Report and Written Opinion for Application No. PCT/US2006/030808, dated Aug. 6, 2007, 10 pages.

* cited by examiner

*Primary Examiner*—Edward Raymond
(74) *Attorney, Agent, or Firm*—Lee & Hayes, PLLC (57) ABSTRACT

A method for monitoring damage to a structure having an actuator and a sensor. The method includes exciting the actuator across a predetermined frequency range to excite the structure, measuring a vibrational characteristic of the structure across the predetermined frequency range in response to the excitation of the actuator using the sensor, calculating a transfer function for the actuator and the sensor using the measured vibrational characteristic, determining a change in the vibrational characteristic across the predetermined frequency range using the transfer function, and analyzing the determined change in the vibrational characteristic across the predetermined frequency range to facilitate determining whether the structure is damaged.

20 Claims, 9 Drawing Sheets

METHOD AND SYSTEM FOR MONITORING STRUCTURAL DAMAGE

BACKGROUND OF THE INVENTION

The present invention relates generally to structural health monitoring, and more specifically to methods and systems for monitoring the structural health of a structure to detect, localize, and assess the severity of damage to the structure.

Some structures (e.g., vehicles such as aircraft) include automated structural health monitoring (SHM) systems having "smart" sensors and actuators integrated into the structure to provide a "built-in-test" (BIT) diagnostic capability. Such "smart structures" may facilitate a reduction of acquisition and life cycle costs. For example, a reliable SHM system may enable condition-based maintenance (CBM), which may reduce life cycle costs by eliminating unnecessary inspections, minimizing inspection time and effort, and extending the useful life of new and aging structural components. Specifically, an integrated SHM system may provide a first level, qualitative damage detection, localization, and assessment capability signaling the presence of structural damage and roughly localizing an area where more precise quantitative non-destructive evaluation may be desired.

Some SHM systems use "passive" strain tracking or acoustic emission monitoring techniques. However, to detect damage both passive strain tracking and passive acoustic emission monitoring techniques may require continuous monitoring. Accordingly, if a power failure or power shut-down occurs, the SHM system may be disabled. Moreover, both passive strain tracking and passive acoustic emission monitoring may not be as sensitive as desired, and therefore may be less accurate and/or reliable. The accuracy and reliability of the acoustic emission monitoring technique may also be compromised by the generally noisy environment of a vehicle. Another possible disadvantage of acoustic emission monitoring is that a large amount of data storage may be necessary. To quantify and localize the damage, the strain tracking technique may require a finite element strain distribution model with which to compare the measured strain distribution across the structure, possibly increasing development cost.

Other known SHM systems may be considered "active" systems because they use transducers to actively excite and sense vibrational characteristics of the structure. The vibrational characteristics are then compared with that of a normal undamaged structure and the difference is used to determine the health of the structure. Specifically, in some known SHM systems, the vibrational characteristics are characterized by computing the transfer function between each actuator and sensor. The transfer functions are compared to a baseline reference representing a normal "healthy" state of the structure. The baseline may be generated by collecting several sets of actuator/sensor data when the structure is healthy, and computing the mean and standard deviation of the data sets. However, temperature variations of the structure may cause these active SHM systems to erroneously detect damage. Specifically, temperature variations in the structure may cause variations in the measured vibrational characteristics that carry over into the transfer functions computed therefrom.

SUMMARY OF THE INVENTION

In one aspect, a method is provided for monitoring damage to a structure having an actuator and a sensor. The method includes exciting the actuator across a predetermined frequency range to excite the structure, measuring a vibrational characteristic of the structure across the predetermined frequency range in response to the excitation of the actuator using the sensor, calculating a transfer function for the sensor using the measured vibrational characteristic, determining a change in the vibrational characteristic across the predetermined frequency range using the transfer function, and analyzing the determined change in the vibrational characteristic across the predetermined frequency range to facilitate determining whether the structure is damaged.

In another aspect, the present invention includes a system for monitoring damage to a structure. The system includes an actuator operatively connected to the structure to excite the structure and a sensor operatively connected to the structure to measure a vibrational characteristic of the structure in response to excitation of the structure. The system also includes a processor operatively connected to the actuator and the sensor programmed to excite the actuator across a predetermined frequency range to excite the structure, receive from the sensor a measured vibrational characteristic of the structure across the predetermined frequency range in response to the excitation of the actuator, calculate a transfer function for the sensor using the measured vibrational characteristic, determine a change in vibrational characteristic across the predetermined frequency range using the transfer function, and analyze the determined change in vibrational characteristic across the predetermined frequency range to facilitate determining whether the structure is damaged.

Other features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Figure 1:
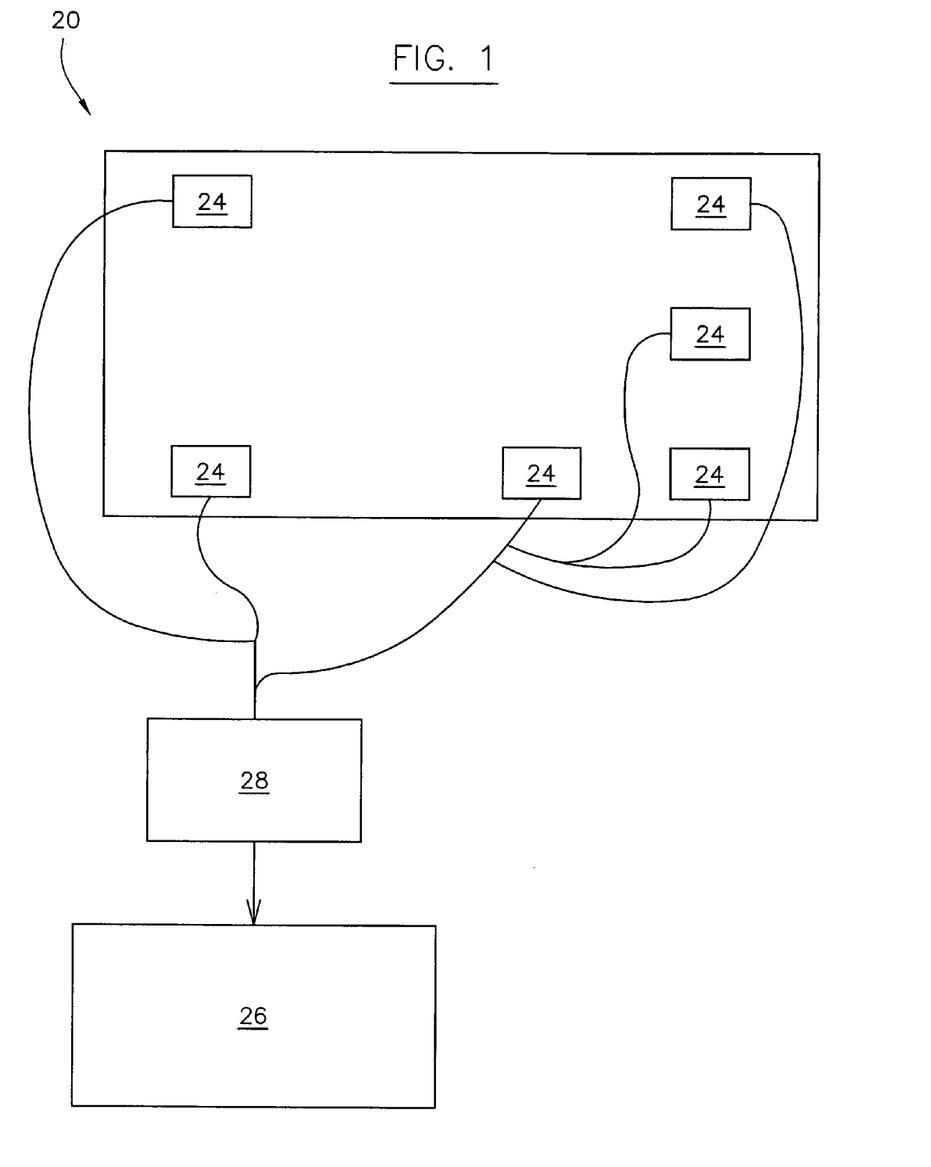
FIG. 1 is a schematic of one embodiment of a structural health monitoring system (SHMS) for monitoring the health of an exemplary structure.

Referring now to the drawings, and in particular to FIG. 1, a structural health monitoring system (SHMS) is designated in its entirety by the reference numeral 20. The SHMS 20 includes a plurality of transducers 24 mountable on a structure 22 (e.g., an aircraft door) and a processor 26 operatively connected to the transducers 24. The transducers 24 each act as a sensor and/or an actuator, when mounted thereon, for exciting the structure 22 and sensing vibrational characteristics (e.g., frequency) of the structure in response to the excitation. Any number and type of transducers 24 may be used. Further, the transducers 24 may be mounted in any location without departing from the scope of the present invention. Additionally, although other actuators and/or sensors may be used, in some embodiments, the transducers 24 are piezoelectric (PZT) transducers capable of both exciting and sensing.

The transducers 24 sense an amplitude of a vibration signal at a predetermined sample rate (e.g., about 50 kHz). The sensed signal, when paired with the corresponding input signal from the actuating transducer, can be transformed into a frequency domain providing gain and phase as functions of frequency. These data, whether in the time domain or the frequency domain, can be statistically analyzed. Although any sample rate and excitation type may be used, in one embodiment the transducers 24 (actuators) excite the structure 22 with a "uniform random" excitation (also known as broadband excitation) at about 50 kHz providing data in a frequency range of between about zero kHz to about 25 kHz. Additionally, although other types of excitation may be used, in one embodiment the transducers 24 (actuators) are excited using chirp excitation.

Although the processor 26 may be mounted on the structure 22, in some embodiments the processor 26 is not mounted on the structure 22. Additionally, in some embodiments the processor 26 is operatively connected to the transducers 24 via an interface 28. An excitation signal source (not shown) for exciting the transducers 24 (actuators) over a predetermined frequency range to thereby excite the structure is operatively connected to at least one of the processor 26 and the interface 28 (if included in the SHMS 20). The interface 28 may also include components (not shown) performing data acquisition functions such as, but not limited to, analog-to-digital conversion. For example, in some embodiments the interface 28 includes a commercial off-the-shelf (COTS) plug-in analog to digital data acquisition board operatively connected to the transducers 24 and the processor 26. In some embodiments, the processor 26 performs data acquisition functions, such as, but not limited to, analog-to-digital conversion. The processor 26 includes appropriate logic (software) for executing any steps, operations, processes, calculations, determinations, algorithms, etc. described and/or illustrated herein. Although other software may be used, in some embodiments the processor includes MATLAB® software from The MathWorks, Inc., of Natick, Mass. 01760-2098 for executing any steps, operations, processes, calculations, determinations, algorithms, etc. described and/or illustrated herein. In some embodiments, the SHMS 20 is configured to be used for monitoring the health of structures (e.g., the structure 22) at a location wherein the structure operates, is maintained, and/or is stored (sometimes referred to as field-testing), such as, but not limited to, configuring a size, shape, weight, and/or durability of the SHMS 20.

Figure 2:
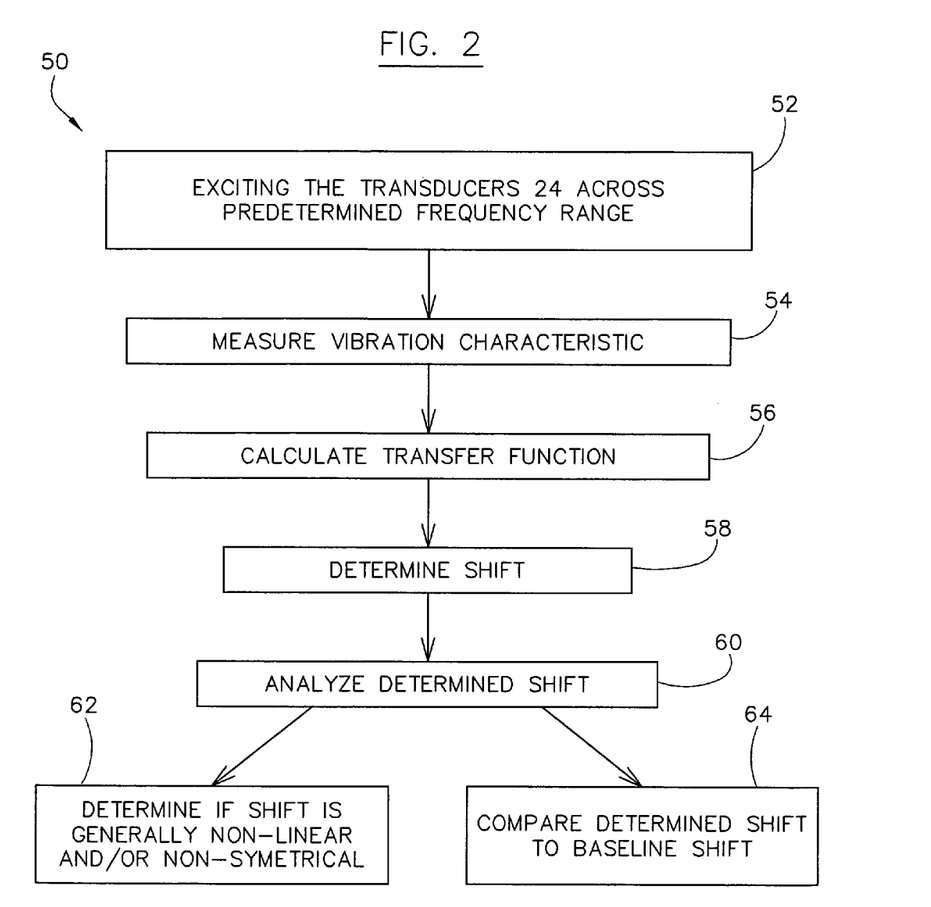
FIG. 2 is a flowchart illustrating one embodiment of a method of monitoring damage to the structure shown in FIG. 1.

As shown in FIG. 2, one embodiment of a method for monitoring damage to a structure (e.g., the structure 22 shown in FIG. 1) is designated in its entirety by the reference numeral 50. Although the method 50 may be performed using other systems and/or components, in some embodiments the method 50 is at least partially performed using SHMS 20 (shown in FIG. 1). Accordingly, and for exemplary purposes only, the method 50 will be described herein as being performed by the SHMS 20. Moreover, and for exemplary purposes only, the method 50 will be described herein with respect to the structure 22. Generally, the method 50 includes exciting one or more of the transducer(s) 24 (shown in FIG. 1) across a predetermined frequency range to thereby excite the structure 22; measuring a vibrational characteristic of the structure 22 in response to the excitation of the transducer(s) 24 across the predetermined frequency range using one or more of the transducer(s) 24; calculating a transfer function for one or more of the transducer(s) 24 using the measured characteristic; determining a change (e.g., a shift) in the vibrational characteristic across the predetermined frequency range using the transfer function; and analyzing the determined change in the vibrational characteristic across the predetermined frequency range to facilitate determining whether the structure 22 is damaged.

One specific example of the method 50 is illustrated in FIG. 2 and described with respect to an embodiment of the SHMS 20 wherein the SHMS includes transducers 24 that sense and excite. Accordingly, the structure 22 is excited at generally the same location where the vibrational characteristic is measured. Of course, in some embodiments, separate transducers 24 are used for exciting and sensing. In these embodiments, the structure 22 is excited at a different location than the vibrational characteristic sensed. As shown in FIG. 2, the method 50 includes exciting 52 each of the transducers 24 one at a time across a predetermined frequency range thereby exciting the structure 22. For example, in one embodiment the method 50 includes exciting 52 two or more of the transducers 24 sequentially. In some embodiments, uniform random excitation of the transducers 24 at a particular sample rate excites the structure 22 at all frequencies between about 0 kHz and half the sample rate. Although any sample rate may be used, in some embodiments the transducers 24 are excited 52 at about 50 kHz. Although the transducers 24 may be excited for any time period, in some embodiments the transducers 24 are excited for less than about one second. Additionally, although other types of excitation may be used, in one embodiment the transducers 24 are excited using broadband excitation of white noise (random) excitation and/or chirp excitation.

In response to the excitation 52, the transducers 24 may measure 54 a vibrational characteristic of the structure 22 across the predetermined frequency range (of the transducers 24). For exemplary purposes only, the vibrational characteristic will be selected as a frequency with respect to the method 50 described and illustrated herein. However, it should be understood that other vibrational characteristics may be used in addition to or in place of frequency with respect to the method 50 described and/or illustrated herein. As an example of the measurement 54, in some embodiments each of the transducers 24 are excited 52 and the frequency response of the structure 22 across the predetermined frequency range (of the transducers 24) is measured 54 at each of the other transducers. For example, as shown in FIG. 1 the SHMS 20 includes six transducers 24 mounted on the structure 22. Each of the six transducers 24 is excited 52 (FIG. 2) across the predetermined frequency range and the frequency response of the structure 22 is measured 54 (FIG. 2) at each of the other five transducers, generating 30 data sets. In some embodiments, each of the transducers 24 produces an analog signal representing the measurement 54 of such transducer and may be digitized by the interface 28 and/or the processor 26.

As shown in FIG. 2, once the response of the structure 22 has been measured 54, a transfer function for one or more measurement(s) 54 of the transducers 24 is then calculated 56 by the processor 26 using the measurement. For example, in some embodiments wherein each of the transducers 24 is excited 52 and the response of the structure 22 is measured 54 at each of the other transducers, calculating 56 a transfer function includes calculating a transfer function for each sensor/actuator pair of the transducers 24. In other words, in some embodiments, each transducer 24 measures 54 the response of the structure 22 to excitation of each of the other transducers, and a transfer function is calculated 56 for each measurement 54 of each transducer. For example, in the exemplary embodiment shown in FIG. 1 wherein the SHMS 20 includes six transducers 24 that generate 30 sets of data, a transfer function is calculated 56 for each data set. In some embodiments, the transfer functions include magnitude and/or phase information for the vibrational characteristic (e.g., frequency). Moreover, in some embodiments the transfer function is a Fast Fourier Transform (FFT). For example, in the exemplary embodiment shown in FIG. 1 the SHMS 20 includes six transducers 24 that generate 30 sets of data, and a transfer function is calculated 56 for each set of data, magnitude and/or phase information from the transfer functions may be saved into an array, for example having 2048 points and a resolution of 12.2 Hz over a predetermined frequency range of about zero and about 25 kHz.

Figure 3:
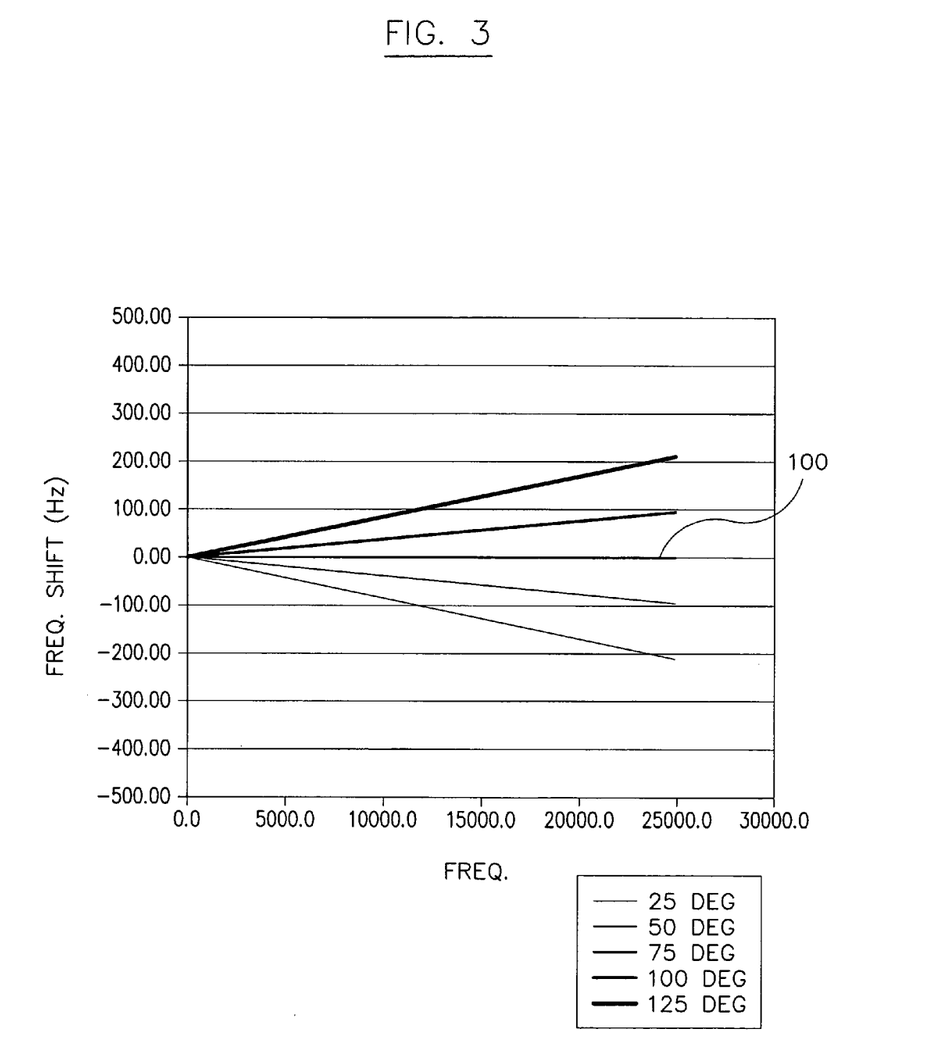
FIG. 3 is a graph illustrating an exemplary frequency change in various temperatures of the structure shown in FIG. 1 across a predetermined frequency range when the structure is undamaged.

Once a transfer function has been calculated 56 for one or more time series measurement(s) 54, the method 50 includes determining 58 a change in one or more of the frequency response(s) 54 using the processor 26. For example, in some embodiments in which a transfer function has been calculated for each time series measurement 54 of each transducer 24, an amount of shift in the peaks of the frequency response as a function of frequency (as compared to a baseline frequency response) is determined 58 for each calculated transfer function. The shifts of each of the calculated transfer functions at various temperature conditions can then be grouped together to illustrate a change in the frequency response of the structure 22 across the predetermined frequency range (of the transducers 24), as shown in FIG. 3. Thus, FIG. 3 represents the frequency shift (as a function of frequency and at various temperature conditions) of one actuator/sensor pair from its baseline condition.

Figure 4:
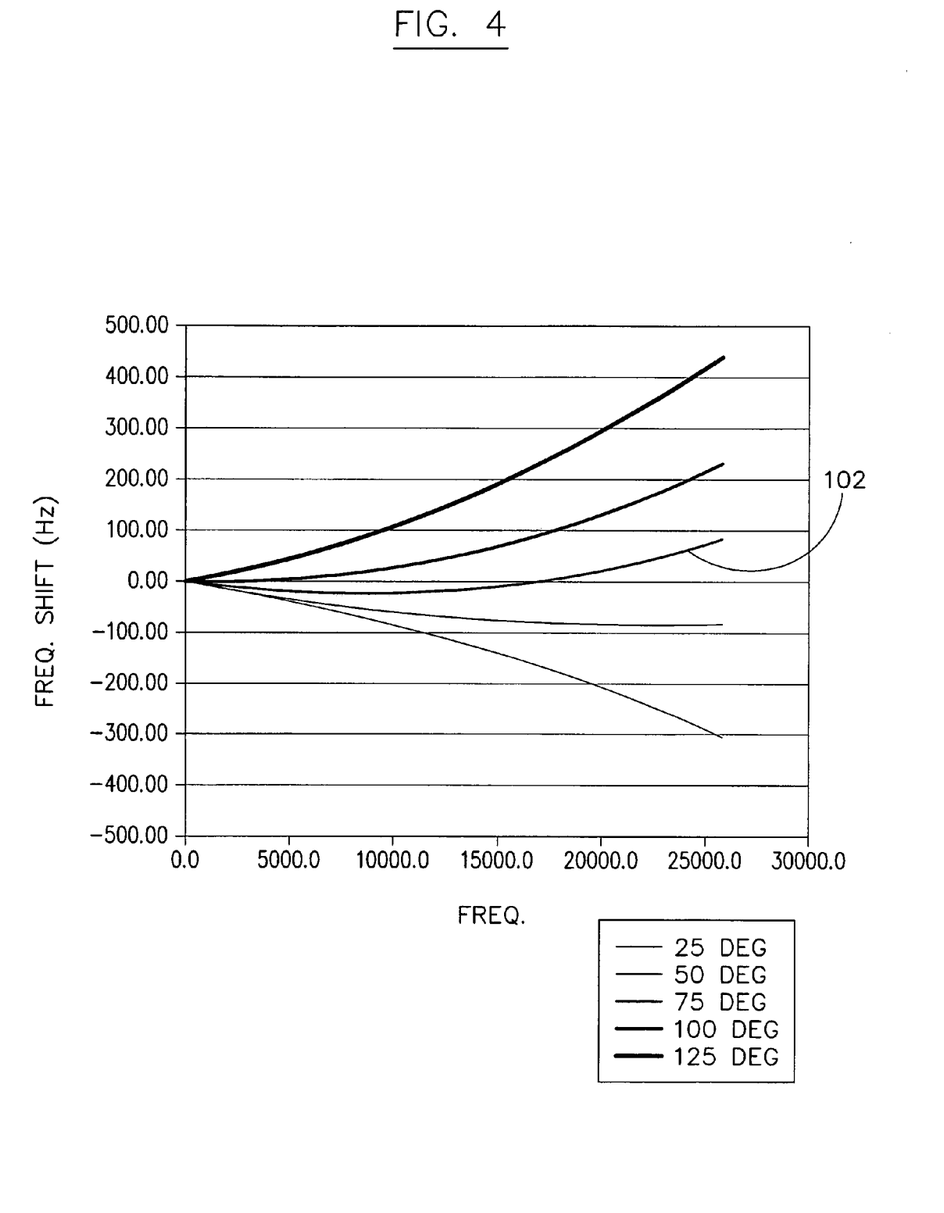
FIG. 4 is a graph illustrating an exemplary frequency change in various temperatures of the structure shown in FIG. 1 across a predetermined frequency range when the structure is damaged.

As discussed herein, vibrational characteristics of the structure 22 (FIG. 1) may facilitate determining whether the structure 22 is damaged. For example, differences between the vibrational characteristics of the structure 22 as measured (e.g., an any time after operation of the structure 22) and the characteristics of a normal "healthy" state of the structure may indicate damage to the structure. However, temperature variations of the structure 22 may cause false indications of damage. For example, when the structure 22 is at a different temperature than a temperature of the structure at which the vibrational characteristics of the normal "healthy" state were determined, the measured vibrational characteristics are different than the determined "healthy" characteristics, and therefore the structure may appear damaged even if it is not damaged. It should be noted that such temperature induced changes to the vibrational characteristics of the structure 22 may carry over into any calculated transfer functions. In some structures, as the temperature of the structure increases, the structure may lose stiffness and consequently the frequency response of the structure may compress (shift negatively) over a range of excitation frequencies. Similarly, in some structures as the temperature of the structure decreases, the structure may become stiffer and consequently the frequency response of the structure may stretch (shift positively) over a range of excitation frequencies. Accordingly, the measured 54 (FIG. 2) frequency response of the structure 22 may shift across the predetermined frequency range (of the transducers 24) depending upon a temperature of the structure, as shown in FIGS. 3 and 4.

As described above and shown in FIG. 2, the method 50 may include determining 58 a nature of such a change or shift in the frequency response of the structure 22. Although the magnitude and nature of the change can be determined 58 using any method, logic, algorithm, equation, etc., in some embodiments the change is determined 58 using Shift(Freq) $=(Coef_1 \times Freq^2)+(Coef_2 \times Freq)+Coef_3$. Although other methods may be used, in some embodiments, $Coef_1$, $Coef_2$, and $Coef_3$ are determined by (1) choosing an initial value for $Coef_1$, $Coef_2$, and $Coef_3$; (2) shifting a frequency interval of the structure 22 by adding Shift(Freq) hertz at each frequency interval across the predetermined frequency range (of the transducers 24); (3) interpolating the transfer function frequency interval back into the original FFT frequency interval to produce a "shifted" transfer function; (4) calculating a difference between the shifted transfer function and a baseline transfer function by summing a magnitude difference at each frequency interval across the predetermined frequency range (of the transducers); and (5) optimizing $Coef_1$, $Coef_2$, and $Coef_3$ to facilitate reducing the difference between the shifted sample transfer function and the baseline transfer function. Although other methods may be used, in some embodiments $Coef_1$, $Coef_2$, and $Coef_3$ are optimized using Powell's Direction Set Methods in Multi-dimensions.

The determined 58 shift equation can then be analyzed 60 to facilitate determining if the structure 22 is damaged. Although the determined 58 shift may be analyzed 60 using any method, logic, algorithm, equation, comparison, etc., in some embodiments analyzing 60 the determined 58 shift includes determining 62 whether the shift equation is generally non-linear. For example, in some embodiments the change in the frequency response of the structure 22 across the predetermined frequency range is generally non-linear when the structure is damaged, as shown in FIG. 4, and is generally linear when the structure is undamaged, as shown in FIG. 3.

A large $Coef_1$ may indicate damage to the structure 22 because $Coef_1$ represents an amount of non-linearity in the shift. For example, when $Coef_1$ is near zero, the shift equation has a nearly linear output indicating no damage and produces straight lines similar to those shown in FIG. 3. When $Coef_1$ has a large magnitude (indicating damage), the shift equation produces non-linear curves such as shown in FIG. 4.

The frequency response of the structure 22 across the predetermined frequency range (of the transducers 24) may be compared 64 with the baseline in any way, some of which should be evident from the baseline shift examples described above, to determine whether the structure is damaged.

Although the determined 58 change in the frequency response of the structure 22 across the predetermined frequency range (of the transducers 24) may be calculated with respect to the baseline in any way, in some embodiments wherein the baseline shift is determined using Shift(Freq)= $(Coef_1 \times Freq^2)+(Coef_2 \times Freq)+Coef_3$, the $Coef_1$ of the determined 58 change in the frequency response of the structure 22 across the predetermined frequency range (of the transducers 24) is compared with the $Coef_1$ of a baseline shift (which may be referred to herein as a "threshold" $Coef_1$). $Coef_1$ therefore may be referred to herein as a damage indicator. In some embodiments, the threshold $Coef_1$ may be determined using a plurality of baseline shifts, for example, using an average, a mean, and/or a standard deviation of a plurality of baseline shifts, and more specifically a $Coef_1$ from a plurality of baseline shifts. Although any comparison 64 may be used in some embodiments the structure 22 is determined to be damaged when the $Coef_1$ of the determined 58 change in the frequency response of the structure 22 across the predetermined frequency range (of the transducers 24) divided by the threshold $Coef_1$ is greater than about one. Of course, in some embodiments $Coef_2$ and/or $Coef_3$ between the determined 58 shift and the baseline shift may be compared.

Figure 5:
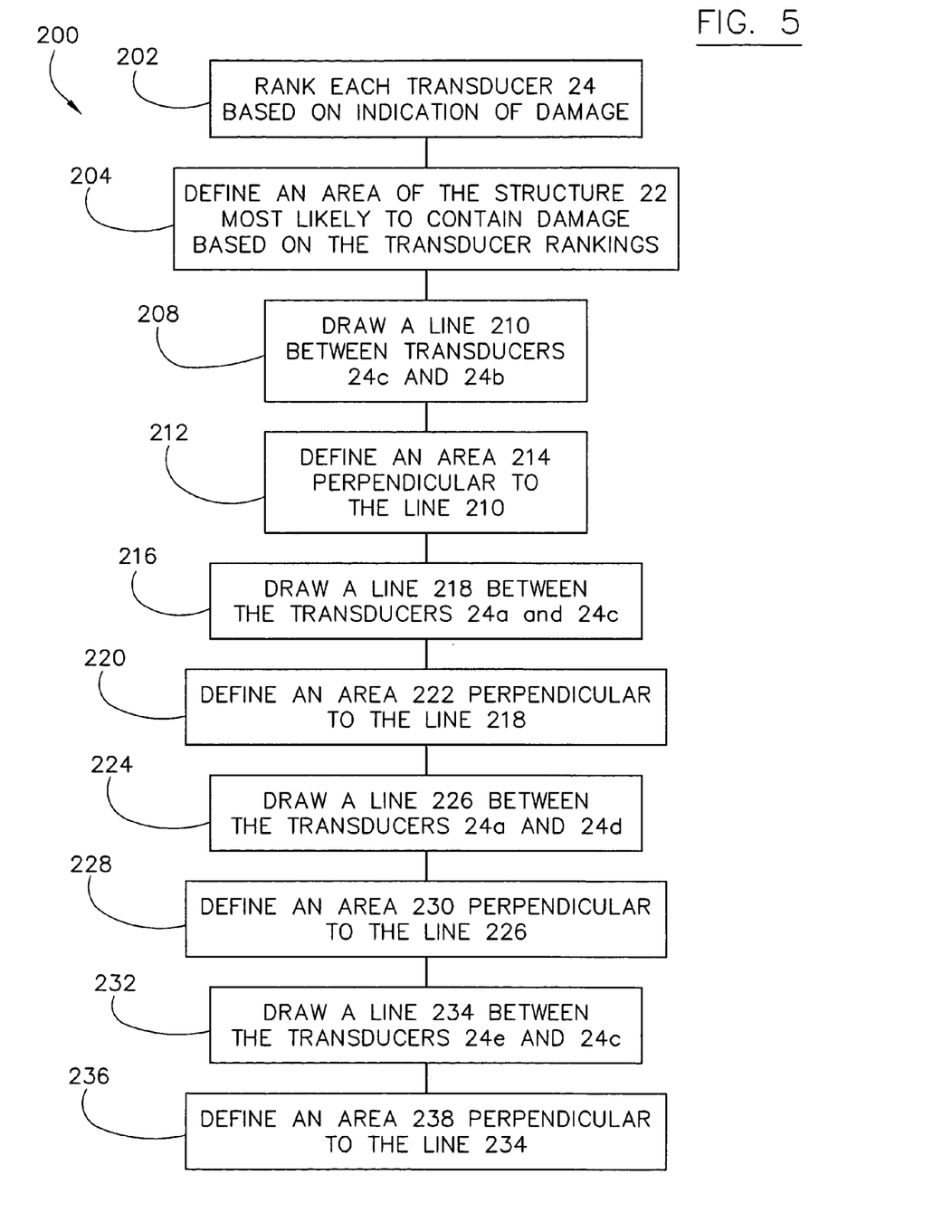
FIG. 5 is a flowchart illustrating one embodiment of a method of locating damage on the structure shown in FIG. 1.

Once a structure has been determined to be damaged, the location of such damage may be found. As shown in FIG. 5, an exemplary embodiment of a method for determining (at least partially using, for example, the SHMS 20 (FIG. 1)) a damage location on a structure (e.g., the structure 22 shown in FIG. 1) is designated in its entirety by the reference numeral 200. The transducers 24 may be sensitive to damage occurring between two of the transducers or anywhere perpendicular to a line drawn between two transducers. This may be, in some embodiments, especially true for the damage indicator $Coef_1$. Generally, in some embodiments, the method 200 includes ranking 202 each of the transducers 24 based on an indication of damage for each transducer pair based on the determined 58 (FIG. 2) change in the frequency response of each transducer pair, and defining 204 an area of the structure 22 most likely to contain damage based on the transducer 24 rankings.

Figure 6:
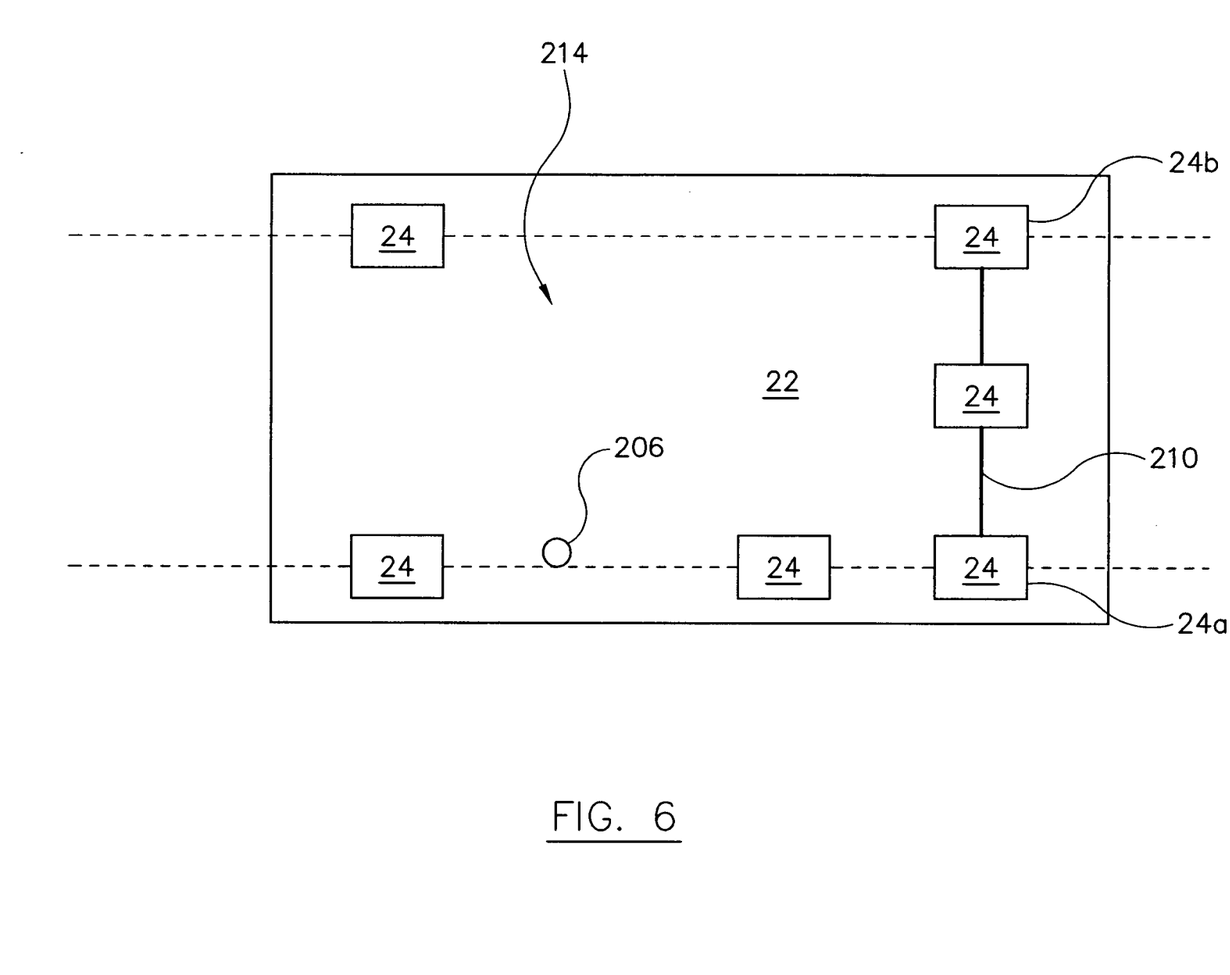
FIG. 6 is a schematic of the structure shown in FIG. 1 illustrating the method shown in FIG. 5.
Figure 7:
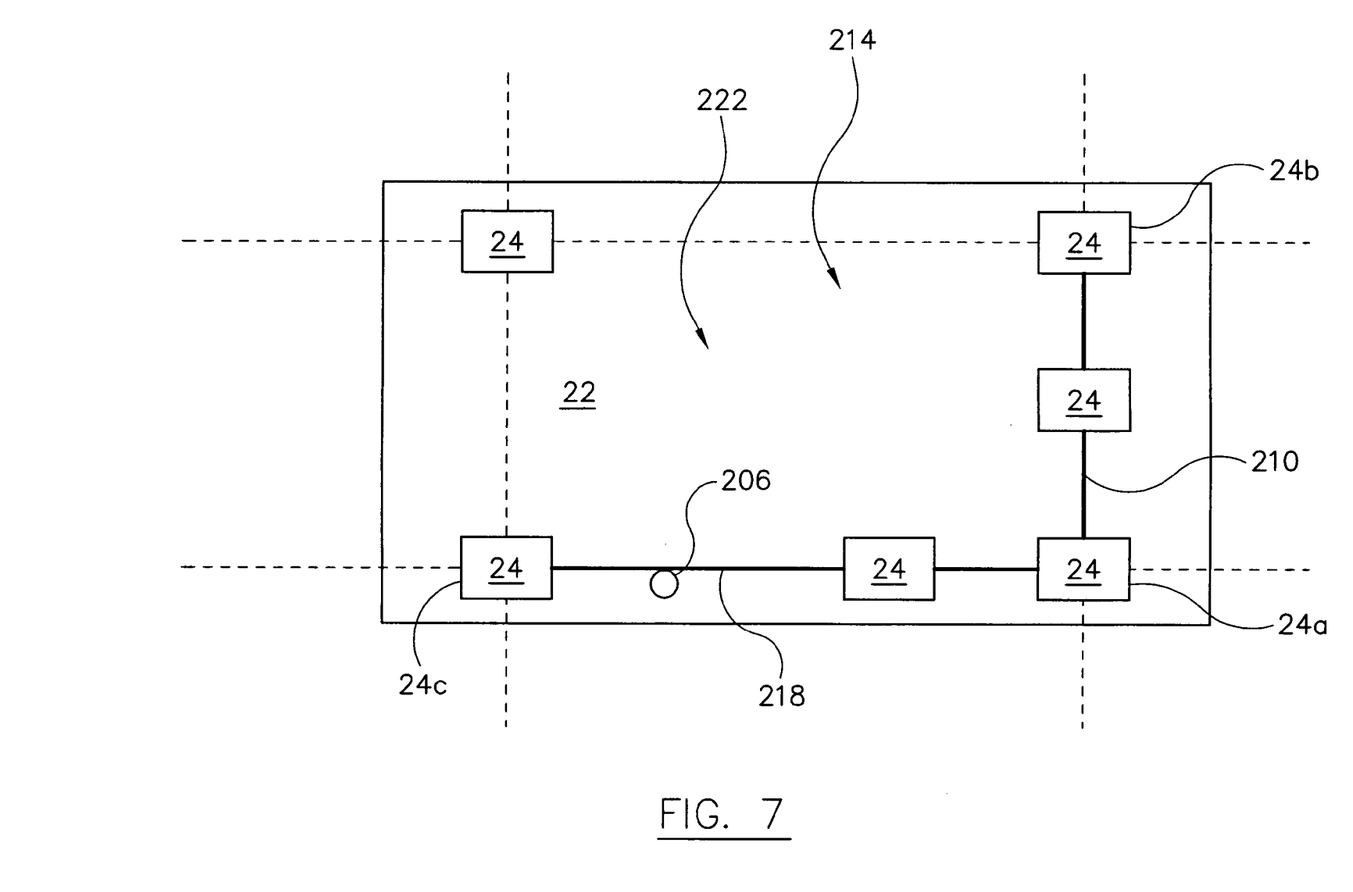
FIG. 7 is another schematic of the structure shown in FIG. 1 illustrating the method shown in FIG. 5.
Figure 8:
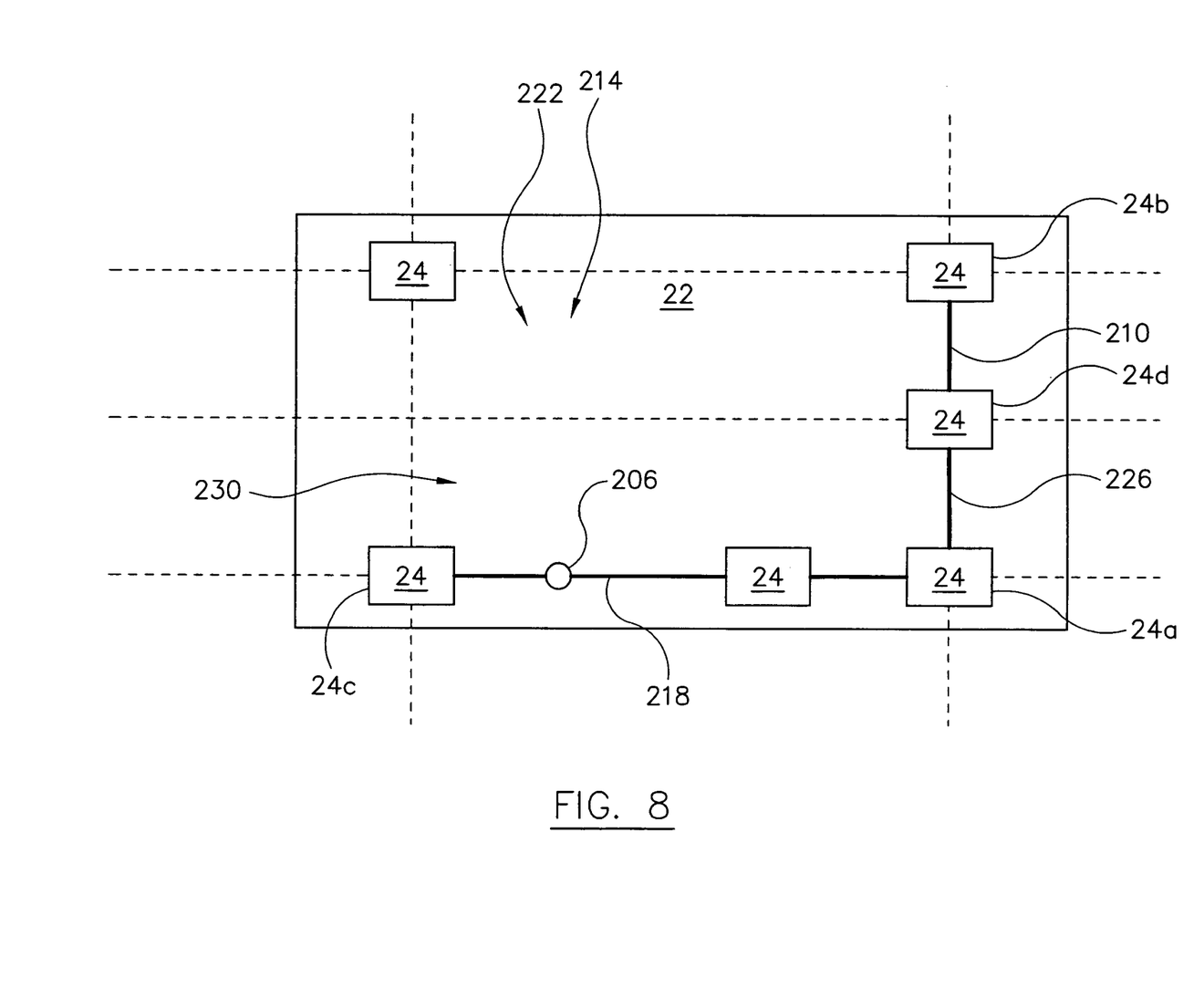
FIG. 8 is yet another schematic of the structure shown in FIG. 1 illustrating the method shown in FIG. 5.
Figure 9:
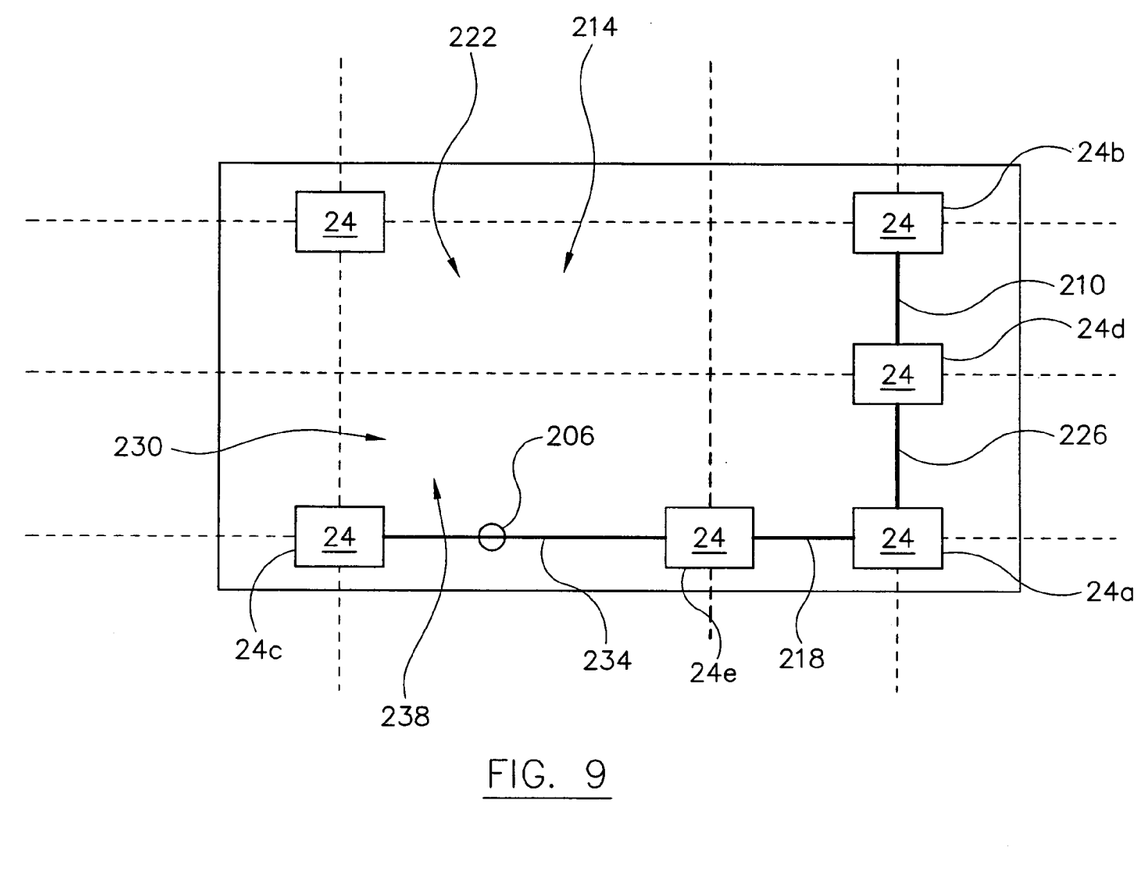
FIG. 9 is still another schematic of the structure shown in FIG. 1 illustrating the method shown in FIG. 5.

For example, a damage location 206 on the structure 22 is shown in FIG. 1. For the specific example of the damage location 206, the highest indication of damage (e.g., using the method 50 (FIG. 2) and the ranking step 202) is between a transducer 24a and a transducer 24b. Accordingly, as shown in FIG. 5, defining 204 an area includes drawing 208 a line 210 between the transducers 24a and 24b and defining 212 an area (generally designated by 214) on the structure 22 perpendicular to the line 210, as shown in FIG. 6. For the specific example of the damage location 206, the second highest damage indication of damage is between a transducer 24c and the transducer 24a. Accordingly, as shown in FIG. 5, defining 204 an area includes drawing 216 a line 218 between the transducers 24a and 24c and defining 220 an area (generally designated by 222) within the area 214, on the structure 22, and perpendicular to the line 218, as shown in FIG. 7. For the specific example of the damage location 206, the third highest damage indication of damage is between a transducer 24d and the transducer 24a. Accordingly, as shown in FIG. 5, defining 204 an area includes drawing 224 a line 226 between the transducers 24a and 24d and defining 228 an area (generally designated by 230) within the area 222, on the structure 22, and perpendicular to the line 226, as shown in FIG. 8. For the specific example of the damage location 206, the fourth highest damage indication of damage is between a transducer 24e and the transducer 24c. Accordingly, as shown in FIG. 5, defining 204 an area includes drawing 232 a line 234 between the transducers 24e and 24c and defining 236 an area (generally designated by 238) within the area 230, on the structure 22, and perpendicular to the line 234, as shown in FIG. 9. As can be seen from FIGS. 6-9, the method 200 facilitates determining a damage location (e.g., damage location 206) by successively narrowing an area of interest on the structure 22 by ranking damage indicators of each of the transducers 24, and more specifically between one or more pairs of transducers 24. Any of the areas 214, 222, 230, and 238 may be referred to herein as a first and/or a second area.

Although the structural health monitoring systems and methods described and/or illustrated herein are described and illustrated herein with respect to a vehicle structure, and more specifically an aircraft door, the systems and methods described and/or illustrated herein are not limited to aircraft doors or vehicle structures generally. Rather, the systems and methods described and/or illustrated herein are applicable to any structure.

Exemplary embodiments of structural health monitoring systems and methods are described above in detail. The systems and methods are not limited to the specific embodiments described herein, but rather, components of each system and steps of each method may be utilized independently and separately from other components and steps described herein. Each structural health monitoring system component and method step can also be used in combination with other structural health monitoring system components and/or method steps.

When introducing elements of the systems and/or methods described and/or illustrated herein and/or embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the embodiments of the present invention, it is intended that all matter contained in the above description and/or shown in the accompanying drawings shall be interpreted as illustrative and not in a limiting sense.

What is claimed is:

1. A method for monitoring damage to a structure having an actuator and a sensor, the method comprising:
    exciting the actuator across a predetermined frequency range to excite the structure;
    measuring a vibrational characteristic of the structure across the predetermined frequency range in response to the excitation of the actuator using the sensor;
    calculating a transfer function for the sensor using the measured vibrational characteristic;
    determining a change in the vibrational characteristic across the predetermined frequency range using the transfer function; and
    analyzing the determined change in the vibrational characteristic across the predetermined frequency range to facilitate determining whether the structure is damaged, wherein analyzing the determined change includes:
        determining an amount of nonlinearity in the determined change using:
        $$Shift(Freq)=(Coef_1 \times Freq^2)+(Coef_2 \times Freq)+Coef_3;$$
        and
        comparing the amount of nonlinearity to a predetermined threshold.

2. A method in accordance with claim 1 wherein the step of analyzing the determined change includes determining whether the change is nonlinear, thereby indicating the structure is damaged.

3. A method in accordance with claim 1 wherein the structure includes a plurality of actuators and a plurality of sensors, and wherein measuring the vibrational characteristic comprises measuring a vibrational characteristic at each sensor, calculating the transfer function comprises calculating a transfer function for each actuator/sensor pair using the measured vibrational characteristics, determining the change comprises determining a change in each calculated transfer function, and analyzing the determined change comprises determining whether the change in each transfer function is nonlinear, thereby indicating the structure is damaged.

4. A method in accordance with claim 1 wherein the method is substantially unaffected by changes in structure temperature.

5. A method in accordance with claim 1 further comprising determining at least one of the $Coef_1$, the $Coef_2$, and the $Coef_3$ by:

choosing an initial value for at least one of the $\text{Coef}_1$, $\text{Coef}_2$, and $\text{Coef}_3$;

shifting a sample transfer function based on at least one of the vibrational characteristic with respect to a baseline vibrational characteristic by adding shift hertz at each frequency interval across the predetermined frequency range;

interpolating a frequency interval of the shifted sample transfer function back into a frequency interval of the unshifted sample transfer function;

calculating a difference between the shifted sample transfer function and a baseline transfer function by summing a magnitude difference at each frequency interval across the predetermined frequency range; and optimizing at least one of the $\text{Coef}_1$, the $\text{Coef}_2$, and the $\text{Coef}_3$ to facilitate reducing the difference between the shifted sample transfer function and the baseline transfer function.

6. A method in accordance with claim 1 wherein comparing the determined the amount of nonlinearity comprises comparing the $\text{Coef}_1$ to a threshold $\text{Coef}_1$.

7. A method in accordance with claim 6 further comprising determining whether the structure is damaged by assessing whether the $\text{Coef}_1$ is greater than the threshold $\text{Coef}_1$.

8. A method in accordance with claim 1 wherein the structure includes a plurality of actuators and a plurality of sensors, each of the sensors being paired with one of the actuators, wherein measuring the vibrational characteristic comprises measuring a vibrational characteristic at each sensor, and wherein the method further comprises:

ranking each of the actuator-sensor pairs based on an indication of damage for each pair based on the determined change in the vibrational characteristic of each pair; and defining an area of the structure most likely to contain damage based on the pair rankings.

9. A method in accordance with claim 8 wherein defining an area of the structure comprises:

defining a first area of the structure extending perpendicular to a line drawn between the highest ranked pairs; and defining a second area of the structure located at least partially within the first area based on the pair rankings.

10. A system for monitoring damage to a structure comprising:

an actuator operatively connected to the structure for exciting the structure;

a sensor operatively connected to the structure for measuring a vibrational characteristic of the structure in response to excitation of the structure; and a processor operatively connected to the actuator and the sensor programmed to:

excite the actuator across a predetermined frequency range to excite the structure;

receive from the sensor a measured vibrational characteristic of the structure across the predetermined frequency range in response to the excitation of the actuator;

calculate a transfer function for the sensor using the measured vibrational characteristic;

determine a change in the vibrational characteristic across the predetermined frequency range using the transfer function; and analyze the determined change in the vibrational characteristic across the predetermined frequency range to facilitate determining whether the structure is damaged, wherein the analysis includes:

determining an amount of nonlinearity in the determined change using: $\text{Shift(Freq)}=(\text{Coef}_1 \times \text{Freq}^2)+(\text{Coef}_2 \times \text{Freq})+\text{Coef}_3$; and comparing the amount of nonlinearity to a predetermined threshold.

11. A system in accordance with claim 10 the processor is programmed to determine whether the change is nonlinear, thereby indicating the structure is damaged.

12. A system in accordance with claim 10 wherein the processor is configured to determine at least one of the $\text{Coef}_1$, the $\text{Coef}_2$, and the $\text{Coef}_3$ by:

choosing an initial value for at least one of $\text{Coef}_1$, $\text{Coef}_2$, and $\text{Coef}_3$;

shifting a sample transfer function based on at least one of the vibrational characteristic with respect to a baseline vibrational characteristic by adding shift hertz at each frequency interval across the predetermined frequency range;

interpolating a frequency interval of the shifted sample transfer function back into a frequency interval of the unshifted sample transfer function;

calculating a difference between the shifted sample transfer function and a baseline transfer function by summing a magnitude difference at each frequency interval across the predetermined frequency range; and optimizing at least one of the $\text{Coef}_1$, $\text{Coef}_2$, and the $\text{Coef}_3$ to facilitate reducing the difference between the shifted sample transfer function and the baseline transfer function.

13. A system in accordance with claim 10 wherein the processor is configured to compare the determined the amount of nonlinearity comprises comparing the $\text{Coef}_1$ to a threshold $\text{Coef}_1$.

14. A system in accordance with claim 13 wherein the processor is configured to determine whether the structure is damaged by assessing whether the $\text{Coef}_1$ is greater than the threshold $\text{Coef}_1$.

15. A system in accordance with claim 10 further comprising a plurality of actuators and a plurality of sensors, each of the sensors being paired with one of the actuators, wherein the processor is configured to:

rank each of the actuator-sensor pairs based on an indication of damage for each pair based on the determined change in the vibrational characteristic of each pair; and define an area of the structure most likely to contain damage based on the pair rankings.

16. A system in accordance with claim 15 wherein the processor is configured to:

define a first area of the structure extending perpendicular to a line drawn between the highest ranked pairs; and define a second area of the structure located at least partially within the first area based on the pair rankings.

17. A method for monitoring damage to a structure having an actuator and a sensor, the method comprising:

exciting each of a plurality of actuators across a predetermined frequency range to excite the structure;

receiving from each of a plurality of sensors a measured vibrational characteristic of the structure across the predetermined frequency range in response to the excitation of the corresponding actuator, wherein each of the sensors being paired with a corresponding actuator;

calculating a transfer function for each sensor using the measured vibrational characteristic;

determining a change in the vibrational characteristic across the predetermined frequency range using the transfer function for each pair;

analyzing the determined change in the vibrational characteristic across the predetermined frequency range for each pair to facilitate determining whether the structure is damaged, wherein a determined nonlinear change indicates the structure is damaged;

ranking each of the actuator-sensor pairs based on an indication of damage for each pair based on an amount of nonlinearity in the determined nonlinear change in the vibrational characteristic of each pair;

defining an area of the structure most likely to contain damage based on the pair rankings, wherein the definition of an area includes:

defining a first area of the structure extending perpendicular to a line drawn between the highest ranked pairs; and defining a second area of the structure located at least partially within the first area based on the pair rankings.

18. A method in accordance with claim 17 wherein the step of ranking each of the actuator-sensor pairs includes determining each amount of nonlinearity by comparing a determined nonlinear change to a corresponding predetermined threshold.

19. A system for monitoring damage to a structure comprising:

a plurality of actuators, each of the actuators operatively connected to the structure for exciting the structure;

a plurality of sensors, each of the sensors being paired with a corresponding actuator, each of the sensors being further operatively connected to the structure for measuring a vibrational characteristic of the structure in response to excitation of the structure; and a processor operatively connected to the plurality of actuator and the plurality of sensors programmed to:

excite each actuator across a predetermined frequency range to excite the structure;

receive from each sensor a measured vibrational characteristic of the structure across the predetermined frequency range in response to the excitation of the corresponding actuator;

calculate a transfer function for each sensor using the measured vibrational characteristic;

determine a change in the vibrational characteristic across the predetermined frequency range using the transfer function for each pair;

analyze the determined change in the vibrational characteristic across the predetermined frequency range for each pair to facilitate determining whether the structure is damaged, wherein a determined nonlinear change indicates the structure is damaged;

rank each of the actuator-sensor pairs based on an indication of damage for each pair based on an amount of nonlinearity in the determined nonlinear change in the vibrational characteristic of each pair;

define an area of the structure most likely to contain damage based on the pair rankings, wherein the definition of an area includes:

define a first area of the structure extending perpendicular to a line drawn between the highest ranked pairs; and define a second area of the structure located at least partially within the first area based on the pair rankings.

20. A system in accordance with claim 19 wherein the processor is configured to determine each amount of nonlinearity by comparing a determined nonlinear change to a corresponding predetermined threshold.

* * * * *